United States Patent [19]

Moldt et al.

[11] Patent Number: 5,444,070

[45] Date of Patent: Aug. 22, 1995

[54] PHENYL SUBSTITUTED HETEROCYCLIC COMPOUNDS

[75] Inventors: Peter Moldt, Humlebæk; Jorgen Scheel-Krüger, Glostrup; Leif H. Jensen, Copenhagen, all of Denmark

[73] Assignee: NeuroSearch A/S, Glostrup, Denmark

[21] Appl. No.: 93,181

[22] Filed: Jul. 16, 1993

[30] Foreign Application Priority Data

Dec. 23, 1992 [DK] Denmark .............................. 1541/92

[51] Int. Cl.⁶ .................. C07D 413/04; C07D 401/04; A61K 31/44
[52] U.S. Cl. ..................... 514/304; 546/125; 546/124
[58] Field of Search .......................... 514/304; 546/125

[56] References Cited

FOREIGN PATENT DOCUMENTS 9309814 5/1993 WIPO .................................. 546/125

OTHER PUBLICATIONS

R. L. Clarke et al., J. Med. Chem. 16(11), 1261–1267 (1973).
F. Ivy Carroll et al., J. Med. Chem. 34, 883–883 (1991).
Meltzer et al., J. Med. Chem. 36(7), 855–862 (1993).
F. Ivy Carroll et al., J. Chem. Soc., Chem. Commun., 44–46 (1993).
F. Ivy Carroll et al., Abstracts of 205th ACS meeting, Denver, Colo., Mar. 28–Apr. 2, 1993, item 84 (Feb. 26, 1993).
van Haaren, F., Elsevier Science Publishers, Chapter 2 by Porsolt et al. (1993), entitled "Methods in Behavioural Pharmacology".
J. F. Teste et al., Fundam. Clin. Pharmacol. 7, 219–226 (1993).

*Primary Examiner*—Alan L. Rotman
*Attorney, Agent, or Firm*—Gordon W. Hueschen

[57] ABSTRACT

The present invention discloses compounds of the formula

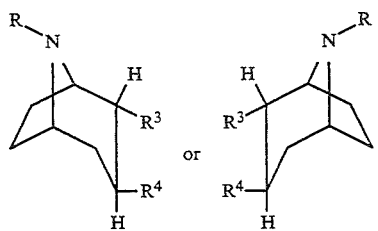

any mixture thereof, or a pharmaceutically acceptable salt thereof; wherein R, $R_3$, and $R^4$ each have the meanings set forth in the specification.

The compounds possess valuable pharmaceutical properties as dopamine reuptake inhibitors.

9 Claims, No Drawings

PHENYL SUBSTITUTED HETEROCYCLIC COMPOUNDS

The present invention relates to: novel tropane derivatives which have pronounced anti drug abuse, antidepressant and anti-Parkinsonian activity and, at the same time, a low degree of undesired side effects; methods for the preparation of the novel tropane derivatives; pharmaceutical compositions containing the novel tropane derivatives; and methods for the treatment of drug abuse, depression and Parkinsonism, by administering a therapeutically effective amount of one or more of the novel tropane derivatives to a living animal body, including a human.

OBJECTS OF THE INVENTION

It is an object of the present invention to provide novel tropane derivatives having anti drug abuse, antidepressant and anti-Parkinsonian activity.

Another object of the invention is to provide novel pharmaceutical compositions containing the novel tropane derivatives which are useful for the treatment of drug abuse, depression and Parkinsonism.

Still another object of the invention is to provide a method of treating drug abuse, depression and Parkinsonism by administering a therapeutically effective amount of one or more of the novel tropane derivatives to a living animal body, including a human.

Other objects will become apparent hereinafter to one skilled in the art.

BACKGROUND OF THE INVENTION

It is well known, that cocaine has a variety of pharmacological actions, primarily a strong CNS stimulation and local anesthetic action. These effects are accompanied by high toxicity and dependence liability. (see for example R. L. Clarke et al in Journal of Medicinal Chemistry 16(11), 1261-1267 (1973). The dependence liability is thought to be related to a combination of cocaine's powerful stimulant activity, short term of action, and rapid onset of action together with its strong dopamine-releasing properties. Further it is well known, that cocaine also possess powerful dopamine reuptake inhibiting activity. It is believed, that compounds having long lasting selective dopamine reuptake-inhibiting properties, and being devoid of dopamine releasing properties, will be extremely useful as a novel type of antidepressant and anti-Parkinsonian agent. Furthermore such compounds will be extremely useful in the treatment of drug addiction, and especially in the treatment of cocaine addiction or misuse.

During the years many attempts have been made to optimize upon the properties of cocaine. Many derivatives of cocaine and of its isomers have been synthesized. See for example R. L. Clarke et al in Journal of Medicinal Chemistry 16(11), 1261-1267 (1973) and F. Ivy Caroll et al in Journal of Medicinal Chemistry 34, 883-886 (1991). Many of these derivatives and probably most pronounced the derivatives of R. L.Clarke et al above are very powerful stimulant compounds and have been found to be very potent dopamine reuptake inhibitors. However none of the cocaine derivatives synthesized until today have been found to be devoid of undesired side effects. R. L.Clarke et al in above paper notes at page 1265, that an enantiomer (trans isomer) of a closely related compound (cis isomer as is cocaine) was not stimulant, and at the same page, that moving a 2-carboxy function from an axial (cis isomer) to an equatorial configuration (trans isomer) gave a compound which was inactive in the locomotor screen (>256 mg/kg), but appeared to produce a slight stimulation. P. C. Meltzer et al in Journal of Medicinal Chemistry, 36(7), 855-862 (1993) notes that the trans isomers are biologically inactive.

Throughout the literature all efforts of derivating cocaine have focused upon optimizing the dopamine reuptake-inhibiting properties and ligand affinity by synthesizing further cis isomers (just as cocaine), undoubtedly because these compounds have been found to be the most potent dopamine reuptake inhibitors as well as the most potent ligands in various binding assays. This also includes the findings published by F. Ivy Carroll et al in J. Chem. Soc. Chem. Commun. pp. 44-46 (1993).

THE PRESENT INVENTION

The inventors to the present invention became scientifically interested in the compounds of R. L. Clarke et al and decided to synthesize the compound designated No, 13 by Clarke et al (Win 35,428). During the syntheses of Win 35,428, the trans isomer of Win 35,428 was isolated as a side product by the present inventors. During a careful characterization of both of these epimeric compounds it was surprisingly noted, that the trans isomer, though being only close to 50 times less potent as compared to the cis isomer (Win 35,428) as a dopamine reuptake inhibitor, then in contrast to Win 35,428, at every relevant dosing level tested appeared essentially or totally devoid of side effects as measured by excitatory locomotor activity and rearing responses as well as by abnormal stereotyped behaviour, and as well as the fact that the compound was essentially free of dopamine releasing properties, all in strong contrast to Win 35,428 and cocaine.

These new and surprising findings prompted the inventors of the present invention to synthesize a large series of derivatives of Win 35,428, its isomers and furthermore more remotely related compounds.

It was thereby surprisingly found that, by selecting the trans isomer, rather than the cis isomer as appearing throughout the literature, and by substituting the $CO_2Me$ group of Win 35,428 for various other substituents and most pronounced for various sterically large substituents, it became possible at one and the same time, to maintain and enhance the dopamine reuptake inhibiting properties of the compounds, as well as to further reduce or eliminate the side effects in the form of excitatory locomotor activity and rearing responses as well as by way of abnormal stereotyped behaviour. Further it was found that the compounds were devoid of dopamine releasing properties. Most surprisingly a strong and potent anti-Parkinsonian and antidepresant activity remained with the compounds.

The invention then, inter alia, comprises the following, alone or in combination:

A method of treating a disorder or disease of a living animal body, including a human, which disorder or disease is responsive to the inhibition of dopamine reuptake, comprising the step of administering to such a living animal body, including a human, in need thereof an effective amount of a compound having the formula

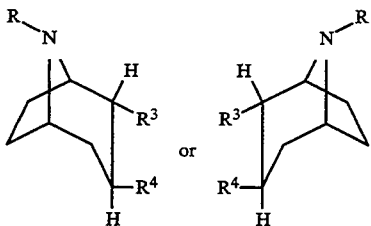

any mixture thereof, or a pharmaceutically acceptable salt thereof; wherein

R is hydrogen, alkyl, alkenyl, alkynyl, cycloalkylalkyl or 2-hydroxyethyl;

$R^3$ is 1,2,4-oxadiazol-3-yl which may by substituted in the 5-position with phenyl which may be substituted one or more times with substituents selected from the group consisting of halogen, $CF_3$, CN, alkoxy, alkyl, alkenyl, alkynyl, amino, nitro, or aryl; phenylphenyl; or benzyl which may be substituted one or more times with substituents selected from the group consisting of halogen, $CF_3$, CN, alkoxy, alkyl, alkenyl, alkynyl, amino, nitro, or aryl; or 1,2,4-oxadiazol-5-yl which may by substituted in the 3-position with phenyl which may be substituted one or more times with substituents selected from the group consisting of halogen, $CF_3$, CN, alkoxy, alkyl, alkenyl, alkynyl, amino, nitro, or aryl; phenylphenyl; or benzyl which may be substituted one or more times with substituents selected from the group consisting of halogen, $CF_3$, CN, alkoxy, alkyl, alkenyl, alkynyl, amino, nitro, or aryl; and $R^4$ is.

phenyl which may be substituted one or more times with substituents selected from the group consisting of halogen, $CF_3$, CN, alkoxy, alkyl, alkenyl, alkynyl, amino, nitro, or aryl;

3,4-methylenedioxyphenyl;

benzyl which may be substituted one or more times with substituents selected from the group consisting of halogen, $CF_3$, CN, alkoxy, alkyl, alkenyl, alkynyl, amino, nitro, or aryl;

aryl which may be substituted one or more times with substituents-selected from the group consisting of halogen, $CF_3$, CN, alkoxy, alkyl, alkenyl, alkynyl, amino, nitro, or aryl; or naphthyl which may be substituted one or more times with substituents selected from the group consisting of halogen, $CF_3$, CN, alkoxy, alkyl, alkenyl, alkynyl, amino, nitro, or aryl; and a method as above, wherein depression or Parkinsonism is treated; and a method as above wherein drug addiction and/or abuse is treated; and a method as above wherein cocaine and/or amphetamine addiction and/or abuse is treated;

the method as first above, wherein the compound employed is (1R,2R,3S)-2-(3-Phenyl-1,2,4-oxadiazol-5-yl)-3-(4-fluorophenyl)tropane, (1R,2R,3S)-2-(3-Phenyl-1,2,4-oxadiazol-5-yl)-3-(4-methylphenyl)-tropane, (1R,2R,3S)-2-(3-Benzyl-1,2,4-oxadiazol-5-yl)-3-(4-fluorophenyl)tropane, (1R,2R,3S)-2-(3-(4-Phenyl-phenyl)-1,2,4-oxadiazol-5-yl)-3-(4-fluorophenyl)tropane, or (1R,2R,3S)-2-(3-Phenyl-1,2,4-oxadiazol-5-yl)-3-(2-naphthyl)tropane, or or a pharmaceutically-acceptable addition salt thereof; and the method as first above, wherein the active ingredient is administered in the form of a pharmaceutical composition thereof, in which it is present together with at least one pharmaceutically-acceptable carrier or diluent; and furthermore a compound having the formula

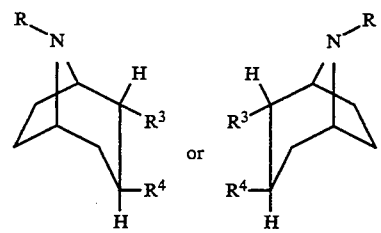

any mixture thereof, or a pharmaceutically acceptable salt thereof; wherein

R is hydrogen, alkyl, alkenyl, alkynyl, cycloalkylalkyl or 2-hydroxyethyl;

R3 is 1,2,4-oxadiazol-3-yl which may by substituted in the 5-position with phenyl which may be substituted one or more times with substituents selected from the group consisting of halogen, $CF_3$, CN, alkoxy, alkyl, alkenyl, alkynyl, amino, nitro, or aryl; phenylphenyl; or benzyl which may be substituted one or more times with substituents selected from the group consisting of halogen, $CF_3$, CN, alkoxy, alkyl, alkenyl, alkynyl, amino, nitro, or aryl; or 1,2,4-oxadiazol-5-yl which may by substituted in the 3-position with phenyl which may be substituted one or more times with substituents selected from the group consisting of halogen, $CF_3$, CN, alkoxy, alkyl, alkenyl, alkynyl, amino, nitro, or aryl; phenylphenyl; or benzyl which may be substituted one or more times with substituents selected from the group consisting of halogen, $CF_3$, CN, alkoxy, alkyl, alkenyl, alkynyl, amino, nitro, or aryl; and $R^4$ is, phenyl which may be substituted one or more times with substituents selected from the group consisting of halogen, $CF_3$, CN, alkoxy, alkyl, alkenyl, alkynyl, amino, nitro, or aryl;

3,4-methylenedioxyphenyl;

benzyl which may be substituted one or more times with substituents selected from the group consisting of halogen, $CF_3$, CN, alkoxy, alkyl, alkenyl, alkynyl, amino, nitro, or aryl;

aryl which may be substituted one or more times with substituents selected from the group consisting of halogen, $CF_3$, CN, alkoxy, alkyl, alkenyl, alkynyl, amino, nitro, or aryl; or naphthyl which may be substituted one or more times with substituents selected from the group consisting of halogen, $CF_3$, CN, alkoxy, alkyl, alkenyl, alkynyl, amino, nitro, or aryl;

and a compound as above which is (1R,2R,3S)-2-(3-Phenyl-1,2,4-oxadiazol-5-yl)-3-(4-fluorophenyl)tropane, (1R,2R,3S)-2-(3-Phenyl-1,2,4-oxadiazol-5-yl)-3-(4-methylphenyl)-tropane, (1R,2R,3S)-2-(3-Benzyl-1,2,4-oxadiazol-5-yl)-3-(4-fluorophenyl)tropane, (1R,2R,3S)-2-(3-(4-Phenyl-phenyl)-1,2,4-oxadiazol-5-yl)-3-(4fluorophenyl)tropane, or (1R,2R,3S)-2-(3-Phenyl-1,2,4-oxadiazol-5-yl)-3-(2-naphthyl)tropane, or or a pharmaceutically-acceptable addition salt thereof; and a pharmaceutical composition, comprising an effective amount of a compound as above, or a pharmaceutically-acceptable addition salt thereof, together with at least one pharmaceutically-acceptable carrier or diluent; and the use of a compound as any above for the manufacture of a medicament for the treatment of a disorder or disease of a living animal body, including a human, which disorder or disease is responsive to the inhibition of dopamine reuptake in the central nervous system.

Examples of pharmaceutically-acceptable addition salts include inorganic and organic acid addition salts such as the hydrochloride, hydrobromide, phosphate; nitrate, perchlorate, sulphate, citrate, lactate, tartrate, maleate, fumarate, mandelate, benzoate, ascorbate, cinnamate, benzenesulfonate, methanesulfonate, stearate, succinate, glutamate, glycollate, toluene-p-sulphonate, formate, malonate, naphthalene-2-sulphonate, salicylate and the acetate. Such salts are formed by procedures well known in the art.

Other acids such as oxalic acid, while not in themselves pharmaceutically acceptable may be useful in the preparation of salts useful as intermediates in obtaining compounds of the invention and their pharmaceutically acceptable acid addition salts.

Halogen is fluorine, chlorine, bromine, or iodine; chlorine and bromine are preferred.

Alkyl means a straight chain or branched chain of one to six carbon atoms or cyclic alkyl of three to seven carbon atoms, including but not limited to, methyl, ethyl, propyl, isopropyl, butyl, isobutyl, t-butyl, pentyl, hexyl, cyclopropyl, cyclobutyl, cyclopentyl, cyclohexyl; methyl, ethyl, propyl and isopropyl are preferred groups.

Alkenyl means a group of two to six carbon atoms, including one double bond, for example, but not limited to ethylene, 1,2- or 2,3-propylene, 1,2-, 2,3-, or 3,4butylene.

Alkynyl means a group of two to six carbon atoms, including one triple bond, for example, but not limited to ethynyl, 2,3-propynyl, 2,3- or 3,4-butynyl.

Cycloalkyl means cycloalkyl of three to seven carbon atoms.

Cycloalkylalkyl means cycloalkyl as above and alkyl as above, meaning for example, cyclopropylmethyl.

Alkoxy is O-alkyl, wherein alkyl is as defined above.

Amino is $NH_2$ or NH-alkyl or N-(alkyl)$_2$, wherein alkyl is as defined above.

Aryl is a 5- or 6-membered heterocyclic monocyclic group. Such an aryl group includes, for example, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1,2,5-thiadiazol4-yl, 2-imidazolyl, 4-imidazolyl, 5-imidazolyl, 2-pyrrolyl, 3-pyrrolyl, 2-furanyl, 3-furanyl, 2-thienyl, 3-thienyl, 2pyridyl, 3-pyridyl, 4-pyridyl.

I.p. means intraperetoneally, which is a well known route of administration.

P.o. means peroral, which is a well known route of administration.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

It will be appreciated by those skilled in the art that some of the compounds of the present invention contain at least one chiral centre and that such compounds exist in the form of a pair of optical isomers (i.e. enantiomers). The invention includes all such isomers and mixtures thereof including racemic mixtures.

Some of the compounds of the present invention exist in (+) and (−) forms as well as in racemic forms. Racemic forms can be resolved into the optical antipodes by known methods, for example, by separation of diastereomeric salts thereof with an optically active acid, and liberating the optically active amine compound by treatment with a base. Another method for resolving racemates into the optical antipodes is based upon chromatography on an optically active matrix. Racemic compounds of the present invention can thus be resolved into their optical antipodes, e.g., by fractional crystallization of d- or l- (tartrates, mandelates, or camphorsulphonate) salts for example. The compounds of the present invention may also be resolved by the formation of diastereomeric amides by reaction of the compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the compounds of the present invention with an optically active chloroformate or the like.

Additional methods for the resolution of optical isomers, known to those skilled in the art may be used, and will be apparent to the average worker skilled in the art. Such methods include those discussed by J. Jaques, A. Collet, and S. Wilen in "Enantiomers, Racemates, and Resolutions", John Wiley and Sons, New York (1981).

Starting materials for the processes described in the present application are known or can be prepared by known processes from commercially available chemicals.

The products of the reactions described herein are isolated by conventional means such as extraction, crystallization, distillation, chromatography, and the like.

The compounds of the invention and their pharmaceutically acceptable derivatives may be prepared by any method known in the art for the preparation of the compounds of the invention and compounds of analogous structure, as shown in the representative examples which follow.

Biology

The compounds of the present invention are potent dopamine reuptake inhibitors.

The compounds of the present invention have been tested for their ability to inhibit reuptake of dopamine in synaptosomes of rat forebrain.

Test procedure

Fresh whole forebrain (at 0°–4° C.) from male Wistar rats (150–200 g) is homogenized in a glass homogenizer with a teflon pestle in 20×volumes 0.32M sucrose. The homogenate is centrifuged at 1000×g (∼2900 rpm) for 10 min. The pellet is discarded and the supernatant is used for uptake assays.

A Krebs Buffer (119 mM NaCl, 24 mM NaHCO$_3$, 2.1 mM KCl, 1.2 mM KH$_2$PO$_4$, 1.8 mM CaCl$_2$, 2 mM MgSO$_4$,7H$_2$O, 12 mM glucose) is equilibrated with an atmosphere of 96% O$_2$: 4% CO$_2$ for at least 60 min at 37° C. To 5 ml Krebs-buffer 100 µl of the radioactivity is added (3H-dopamine 1×10$^{-9}$M final concentration) and 100 µl test substance solution and 200 µl of tissue suspension. The samples are thoroughly mixed and incubated 10 min at 37° C. followed by 2 min at 0° C. After incubation the samples are poured directly onto Whatman GF/C glass fibre filters under suction and immediately washed with 2×5 ml ice-cold 0.9% saline (NaCl) buffer. To the filter is added 3 ml of scintillation fluid, and the amount of radioactivity on the filters is determined by conventional liquid scintillation counting. The test value is given as the IC$_{50}$ (the concentration (µM) of the test substance which inhibits the uptake by 50%). Test results obtained by testing selected compounds of the present invention will appear from the below table:

TABLE

| Compound | Dopamine reuptake inhibiting activity |
|---|---|
| (1R,2R,3S)-2-(3-phenyl-1,2,4-oxadiazol-5-yl)-3-(4-chlorophenyl)-tropane | 0.33 µM |
| (1R,2R,3S)-2-(3-phenyl-1,2,4-oxadiazol-5-yl)-3-(4-methylphenyl)-tropane | 0.96 µM |
| (1R,2R,3S)-2-(3-phenyl-1,2,4-oxadiazol-5-yl)-3-(2-naphthyl)-tropane | 0.54 µM |

The compounds of the present invention have been tested for their antiparkinsonian activity by their ability to antagonize haloperidol-induced catalepsy. This model is recognized in the art as a very reliable model for antiparkinsonian activity.

The Catalepsy test for antiparkinsonian effects.

The principle behind the haloperidol catalepsy test relates to the fact that the drug haloperidol (Serenase ®) induces a receptor blockade of post synaptic dopamine receptors within the dopamine innervated corpus striatum of the rat brain. Following the blockade of active dopamine neurotransmission of the striatum a state of rigid immobility is induced, during which the rat can be placed in various totally abnormal immobile postures involving the forelegs and the whole body. These immobile postures can also be produced by high doses of haloperidol to several other animal species(- mice, dog) as well as primates, including humans. The immobile posture effect induced by haloperidol closely resembles the state of Parkinson's disease in humans, which is due to a deficit of the dopaminergic innervation of the striatal complex (nucleus caudatus, putamen).

The day before testing, the rats weighing 200–250 g are housed 2 and 2 together in standard macroIon cages. The test substance is usually given perorally 1 h before a standard dose of the dopamine antagonist haloperidol 0.25 mg/kg given subcutaneously. The testing for the immobile catalepsy syndrome includes 4 tests performed in the following consecutive order:
1) a vertical wire netting (40×40 cm high).The meshes (openings) of the nettings are approximately 1×2 cm.
2) a horizontal bar 9 cm above the floor
3) a 9 cm high block (bar)
4) a 3 cm high block (cork)

The rats were scored for the immobile cataleptic syndrome every 15 min in all 4 tests starting 15 min after the haloperidol injection. The intensity of catalepsy was tested during 10 sec in all tests and evaluated according to a criteria of 10 sec of total immobility for a score of 2. Minor movements of the head or the body give the score of 1 and a score of 0 is given if the rat shows no symptoms.

The rat was placed in the middle of the vertical wire netting, then on the horizontal bar in an extended position with support by both the forelegs on the bar. The rats were then tested, whether or not they were willing to sit with the left or right forelegs placed first on the 9 and then on the 3 cm block for a duration of 10 sec. The maximum score for all 4 tests is thus a total of 8.

TABLE

| Compound | Minimum effective dose (peroral administration) |
|---|---|
| (1R,2R,3S)-2-(3-phenyl-1,2,4-oxadiazol-5-yl)-3-(4-chlorophenyl)-tropane | 0.25 mg/kg |
| (1R,2R,3S)-2-(3-phenyl-1,2,4-oxadiazol-5-yl)-3-(4-methylphenyl)-tropane | 1.0 mg/kg |
| (1R,2R,3S)-2-(3-phenyl-1,2,4-oxadiazol-5-yl)-3-(2-naphthyl)-tropane | 0.25 mg/kg |

Side effect profile of the compounds of the present invention

The side effects of cocaine and the central stimulant amphetamine derivatives involve central excitement and stimulation in animals including primates and these effects can also be observed in humans. A serious side effect of cocaine and of the amphetamine derivatives includes also the ability to provoke toxic psychotic symptoms closely resembling the mental disease schizophrenia and these include halucinations, paranoia and abnormal bizarre stereotyped mental activity and stereotyped motor activity.

The current knowledge strongly indicates and suggests that these syndromes in primates and in humans are due to an extensive and massive release of dopamine within the striatal complex and in particular within the mesolimbic dopamine system, which innervate limbic structures including the nucleus accumbens.

The induction of stereotyped abnormal behavior in rodents thus also represents one of the most used animal models of schizophrenia in models for antipsychotic neuroleptic drugs (including haloperidol and chlorpromazine).

The development of toxic abnormal stereotyped amphetamine syndrome as described below may predict a toxic central stimulant side effect of dopamine releasing compounds in humans.

Classification of the behavioural excitatory locomotor and rearing responses after amphetamine, cocaine and various dopamine uptake inhibitors.

Male SPF wistar rats weighing 200–250 g were used for the gross behavioural studies. All rats were transferred the day before the experiments to individual cages made of wire netting (floor area 21×27 cm, height 16 cm) at a room temperature of 21°–23° C. As a rule the rats were observed continuously for 5-6 hrs after the administration of the drugs. The behavioural elements here classified as rearing (i.e. standing up on the hindlegs) and locomotor activities (i.e. forward running activities) were registered, and the maximum peak effects were classified according to the following rating scale:

0 = non-existent or very infrequent
+ = weak and infrequent
+ + = moderate in intensity and frequency
+ + + = very strong, continuous and intense The degree of locomotor activity was also tested and measured quantitatively in photocell activity cages. For the measurement of this locomotor activity 100 g female rats are used.

TABLE

| Compound | Dose(i.p.) | Activity |
|---|---|---|
| (1R,2R,3S)-2-(3-phenyl-1,2,4-oxadiazol-5-yl)-3-(4-chlorophenyl)-tropane | 50 mg/kg | 0 |
| (1R,2R,3S)-2-(3-phenyl-1,2,4-oxadiazol-5-yl)-3-(4-methylphenyl)-tropane | 50 mg/kg | 0 |
| (1R,2R,3S)-2-(3-phenyl-1,2,4-oxadiazol-5-yl)-3-(2-naphthyl)-tropane | 50 | 0 |

Classification of the abnormal stereotyped behaviour.

In general, the abnormal stereotyped behaviour after administration of amphetamine and cocaine-like central stimulant drugs can be classified into "low" and "high" intensity scores of stereotyped behaviour. The low intensity score of stereotypy includes an abnormal and continuous repetition of the locomotor, rearing and sniffing behaviour, and these syndromes are usually seen only after the lower doses of the central dopaminergic central stimulant drugs or may be seen present during the pre- and afterphases of the high doses. The low intensity behavioural effects are here included into the locomotor and rearing syndrome. The high intensity syndrome of stereotypy is here considered, if the behavioural repertoire of the rat becomes strongly restricted in variation and consists of the continuous repetition of one or a few items of behaviour. The syndrome of stereotyped sniffing behaviour is thus performed continuously on only a small restricted area of the cage. This activity usually starts on the upper part of the wall and following higher doses of the drugs increases in intensity to the performance of sniffing towards the lower part of the cage on the wall or on the wires of the floor. During this stage of high intensity stereotypy all normal behavioural elements are absent including behaviour such as eating, drinking, grooming and normal explorative investigation of the environment. In rats, the high intensity sniffing can develop into sniffing associated with licking and/or biting-gnawing activity on the wire netting of the cage following still higher doses of the stimulant drugs. The rats are here usually sitting in a typical crouched posture in a corner of the cage. Backward locomotion may occasionally be observed.

The following rating scale is used for the high intensity stereotypy on the condition that the behavioural syndromes are as decribed above:

+ = only stereotyped sniffing
+ + = stereotyped sniffing and episodic licking
+ + + = Continuous licking and/or biting gnawing

TABLE

| Compound | Dose(i.p.) | Activity |
|---|---|---|
| (1R,2R,3S)-2-(3-phenyl-1,2,4-oxadiazol-5-yl)-3-(4-chlorophenyl)-tropane | 50 mg/kg | 0 |
| (1R,2R,3S)-2-(3-phenyl-1,2,4-oxadiazol-5-yl)-3-(4-methylphenyl)-tropane | 50 mg/kg | 0 |
| (1R,2R,3S)-2-(3-phenyl-1,2,4-oxadiazol-5-yl)-3-(2-naphthyl)-tropane | 50 mg/kg | 0 |

Pharmaceutical Compositions

While it is possible that, for use in therapy, a compound of the invention may be administered as the raw chemical, it is preferable to present the active ingredient as a pharmaceutical formulation.

The invention thus further provides pharmaceutical formulations comprising a compound of the invention or a pharmaceutically acceptable salt or derivative thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutipal formulations include those suitable for oral, rectal, nasal, topical (including buccal and sub-lingual), vaginal or parenteral (including intramuscular, sub-cutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to one hundred (100) milligrams, per tablet, are accordingly suitable representative unit dosage forms.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in admixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

The compounds according to the present invention may thus be formulated for parenteral administration (e.g. by injection, for example bolus injection or continuous infusion) and may be presented in unit dose form in ampoules, prefilled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents; thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example, of the order of 5 microns or less. Such a particle size may be obtained by means known in the art, for example by micronization.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

Method of Treating

The compounds of this invention are extremely useful in the treatment of drug abuse, depression and Parkinsonism due to their potent dopamine uptake-inhibiting activity together with their low degree of undesired side-effects. These properties make the compounds of this invention extremely useful in the treatment of drug abuse, depression and Parkinsonism as well as other disorders sensitive to the dopamine uptake-inhibiting activity of the compounds of the present invention. The compounds of this invention may accordingly be administered to a living animal body, including a human, in need of treatment, alleviation, or elimination of an indication associated with or responsive to dopamine uptake-inhibiting activity. This includes especially drug abuse, depression and Parkinsonism.

Suitable dosage range are 0.1–500 milligrams daily, 10–50 milligrams daily, and especially 10–30 milligrams daily, dependent as usual upon the exact mode of administration, form in which administered, the indication toward which the administration is directed, the subject involved and the body weight of the subject involved, and further the preference and experience of the physician or veterinarian in charge.

The following examples will illustrate the invention further, however, they are not to be construed as limiting.

EXAMPLE 1

(−)-Anhydroecgonine methyl ester.

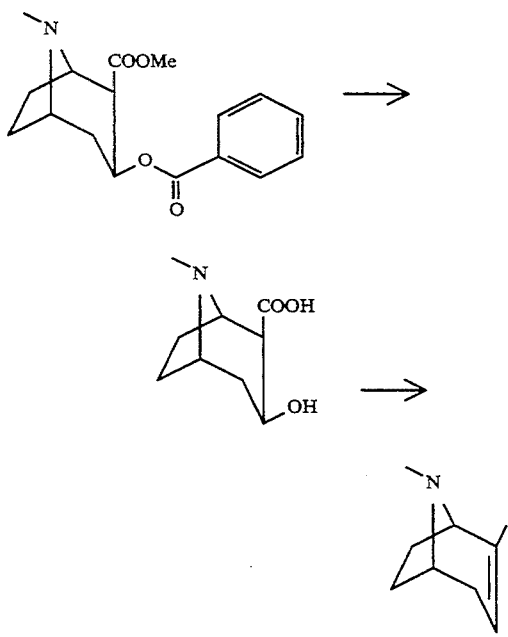

(1R,2R,3S)-2-Carbomethoxy-3-benzoxytropane, hydrochloride (100 g, 0.29 mol) was refluxed in 1000 ml 1M hydrochloric acid for 18 hours and the solution was ice cooled. Benzoic acid was collected by filtration and the filtrate was concentrated in vacuo. Trituration of the remanescens with ethanol and filtration yields (1R,2R,3S)-3-hydroxy-tropane 2 carboxylate, hydrochloride as a white crystalline compound which without further purification was dried and refluxed in phosphorous oxychloride (50 ml) for two hours. The solution was concentrated in vacuo and absolute methanol (150 ml) was slowly added under ice cooling. The solution was stirred at ambient temperature for 16 hours and was concentrated in vacuo. The remanescens was ice cooled and made basic by addition of a sodium hydroxide solution (10M, approximately 100 ml) and was extracted 5 times with diethyl ether. The combined organic phase was dried and concentrated in vacuo yielding an oil, which was distilled in vacuo (70°–74° C., 1 mBar) yielding the title compound as a clear oil.

EXAMPLE 2

(1R,2S,3S)-2-Carbomethoxy-3-(4-fluorophenyl)tropane and (1R,2R,3S)-2-carbomethoxy-3-(4-fluorophenyl)tropane

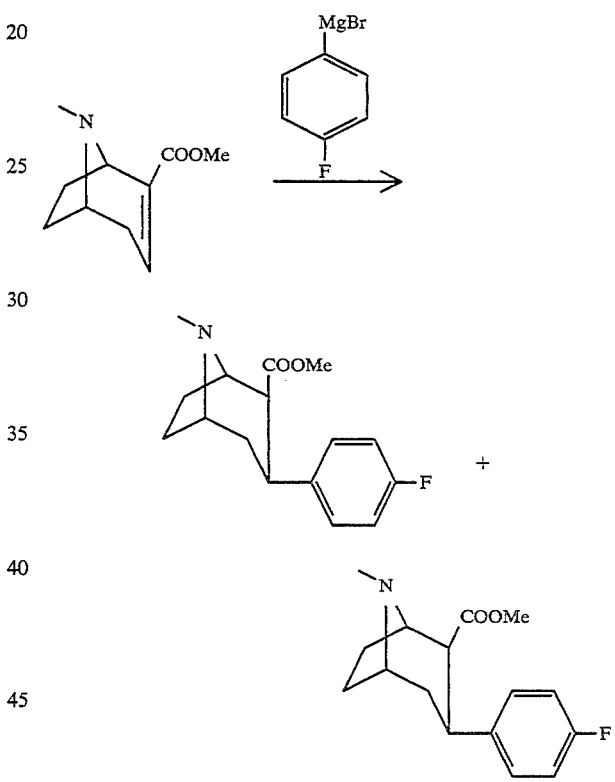

Grignard reagent was made in a three necked reaction flask equipped with mechanical stirring, an intensive condenser and a pressure equilibrated funnel, using 4-bromo-fluorobenzene (27.5 ml, 250 mmol) and magnesium turnings (6.3 g, 260 mmol) in 250 ml absolute diethyl ether. The solution of grignard reagent was cooled to −20° C. and a solution of (−)-anhydroecgonine methyl ester (21.7 g, 120 mmol) in 100 ml absolute diethyl ether was added over ½ hour. The reaction was stirred one hour at −20° C. and the reaction was quenched in one of the following two ways:

1) The reaction mixture was stirred into 250 ml crushed ice and the water phase was made acidic by addition of approximately 100 ml 4M hydrochloric acid. The organic phase was discharged and the water phase was washed with 100 ml diethyl ether. The water phase was made basic by addition of 25% ammonium hydroxide solution, and was then saturated with sodium chloride and was finally extracted three times with diethyl ether. The combined organic phase was dried and concentrated in vacuo yielding an oil which was distilled in vacuo (150°–160° C., 2 mBar). This method yields a mixture of two stereoisomers (2S/2R−⅓) which was separated by column chromatography using a mixture of diethyl ether and pentane (1+1)+1% triethyl amine as eluent. The crude products were triturated in pentane yielding (1R,2S,3S)-2-carbomethoxy-3-(4-fluorophenyl) tropane, white crystals m.p. 91°–92° C. and (1R,2R,3S)-2-carbomethoxy-3-(4-fluorophenyl)tropane, white crystals m.p. 65°–66° C.

2) The reaction mixture was cooled to −78° C. and a solution of trifluoro acetic acid (20 ml, 250 mmol) in 50 ml diethyl ether was added over 10 minutes. The cooling bath was removed and when the temperature has reached 0° C. the mixture was stirred into 700 ml water. The pH of the water phase was adjusted to pH 1 by addition of concentrated hydrochloric acid followed by aqueous work up and purification in the same way as described above. This method yields a mixture of two stereoisomers (2S/2R-2/1 ).

The following compounds were made in a similar way:

(1R,2R,3S)-2-Carbomethoxy-3-benzyltropane and (1R,2S,3S)-2-carbomethoxy -3-benzyltropane, method 2, only (1R,2S,3S)-2-carbomethoxy-3-benzyltropane was obtained without contamination of the other isomer, as an oil, which crystallize upon standing, m.p. 53°–54° C. (1R,2R,3S)-2-carbomethoxy-3-benzyltropane was obtained by isomerisation of the mixture as described below.

(1R,2R,3S)-2-Carbomethoxy-3-(4-chlorophenyl)tropane and (1R,2S,3S)-2-carbomethoxy-3-(4-chlorophenyl)tropane, method 2, the two isomers were not separated but the mixture was isomerized as described below.

(1R,2R,3S)-2-Carbomethoxy-3-(4-chlorophenyl)tropane, (1R,2S,3S)-2-carbomethoxy-3-(4-chlorophenyl)tropane, (1S,2S,3R)-2-carbomethoxy-3-(4-chlorophenyl)tropane and (1S,2R,3R)-2-carbomethoxy-3-(4-chlorophenyl)tropane, method 2, the two sets of enantiomeric pairs were not separated but the mixture was isomerized and hydrolyzed as described below.

(1R,2R,3S)-2-Carbomethoxy-3-(4-methylphenyl)tropane and (1R,2S,3S)-2-carbomethoxy-3-(4-methylphenyl)tropane, method 2, the two isomers were not separated but the mixture was isomerized and hydrolyzed as described below.

(1R,2S,3S)-2-Carbomethoxy-3-(2-naphthyl)tropane and (1R,2R,3S)-2-carbomethoxy-3-(2-naphthyl)tropane, method 2, grignard reagent made by addition of a mixture of one equivalent 2-bromonaphthalene and 1,2-dibromoethane in diethyl ether to a refluxing suspension of two equivalents of magnesium. Both products were white crystalline compounds with m.p. 79°–80° C. and m.p. 86°–87° C. respectively.

(1R,2R,3S)-2-Carbomethoxy-3-(1-naphthyl)tropane and (1R,2S,3S)-2-carbomethoxy-3-(1-naphthyl)tropane, hydrochloride, method 2, grignard reagent made by addition of a mixture of one equivalent 1-bromonaphthalene and 1,2-dibromoethane in diethyl ether to a refluxing suspension of two equivalents of magnesium. The title compounds were isolated as respectively a white crystalline compound, m.p. 133°–135° C. and an amorphous compound.

(1R,2S,3S)-2-Carbomethoxy-3-(3,4-dichlorophenyl)tropane and (1R,2R,3S)-2-carbomethoxy-3-(3,4-dichlorophenyl)tropane, method 2. Both products were white crystalline compounds with m.p. 69°–70° C. and 61°–63° C. respectively.

(1R,2S,3S)-2-Carbomethoxy-3-(4-phenyl-phenyl)tropane and (1R,2R,3S)-2-carbomethoxy-3-(4-phenyl-phenyl)tropane, method 2. Both products were white crystalline compounds with m.p. 130°–132° C. and 95°–96° C. respectively.

(1R,2S,3S)-2-Carbomethoxy-3-(4-t-butyl-phenyl)tropane and (1R,2R,3S)-2-carbomethoxy-3-(4-t butyl-phenyl)tropane, method 2. Both products were white crystalline compounds with m.p. 84°–85° C. and 83°–84° C. respectively.

EXAMPLE 3

(1R,2R,3S)-2-Carbomethoxy-3-benzyltropane, hydrochloride.

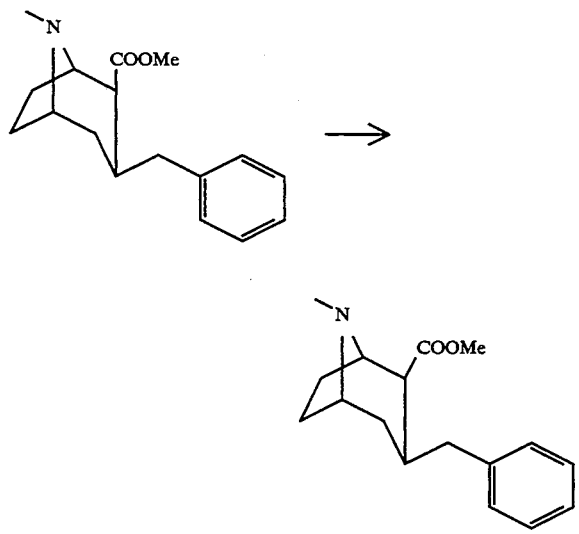

To a solution of (1R,2S,3S)-2-carbomethoxy-3-benzyltropane (5.6 g, 20.5 mmol) in absolute methanol (100 ml) was added a solution of sodium methanolate in methanol (2M, 2 ml) and the mixture was refluxed for 16 hours. The reaction mixture was concentrated in vacuo and the remanescens was dissolved in diethyl ether and was washed with water. The organic phase was dried and concentrated in vacuo. The crude product was purified by column chromatography using a mixture of diethyl ether and pentane (1+1)+1% triethyl amine as eluent yielding (1R,2R,3S)-2-carbomethoxy-3-benzyltropane as an oil. By dissolution of this product in diethyl ether and subsequent addition of a solution of hydrochloric acid in diethyl ether the title compound precipitates as white crystals, m.p. 188°–190° C.

EXAMPLE 4

(1R,2S,3S)-3-(4-Fluorophenyl)tropane 2-carboxylate, hydrochloride.

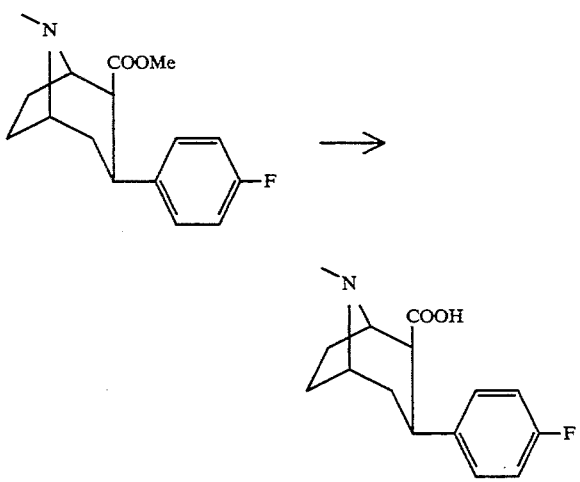

A solution of (1R,2S,3S)-2-carbomethoxy-3-(4-fluorophenyl)tropane (5 g, 18 mmol) in diluted hydrochloric acid (2M, 100 ml) was refluxed for 16 hours and the reactions mixture was concentrated in vacuo. The remanescens was triturated in ethanol and was concentrated in vacuo. Finally the crude product was triturated in cold acetone and the title compound was collected by filtration as white crystals, m.p.258°–260° C.

The following compound was made in a similar way:
(1R,2S,3S)-3-(2-Naphthyl)tropane 2-carboxylate, hydrochloride, yellow crystals.

EXAMPLE 5

(1R,2R,3S)-3-Benzyltropane 2-carboxylate, hydrochloride.

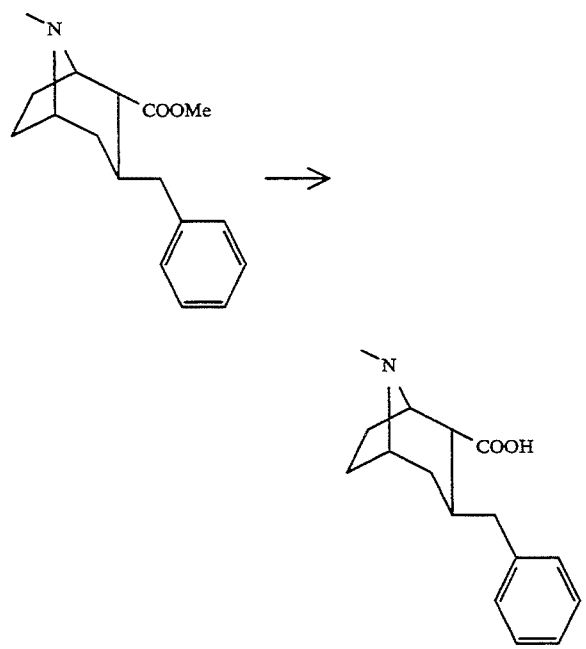

To a solution of (1 R,2R,3S)-2-carbomethoxy-3-benzyltropane (4.15 g, 15.2 mmol) in ethanol (50 ml) was added an aqueous solution of sodium hydroxide (4M, 5 ml) and the mixture was refluxed for 2 hours. The reaction mixture was concentrated in vacuo and the remanescens was dissolved in water and the solution was washed with diethyl ether. The aqueous phase was acidified with concentrated hydrochloric acid and was concentrated in vacuo. Finally the crude product was dissolved in a small amount of methanol and by addition of diethyl ether the title compound precipitates as white crystals, m.p.270°–273° C.

The following compounds were made in a similar way:

(1R,2R,3S)-3-(4-Fluorophenyl)tropane 2-carboxylate, hydrochloride, white crystals, m.p.>300° C.

(1R,2R,3S)-3-(4-Chlorophenyl)tropane 2-carboxylate, hydrochloride, white crystals, m.p. 248°–250° C.

(1R,2R,3S)-3-(4-Chlorophenyl)tropane 2-carboxylate, hydrochloride and (1S2S,3R)-3-(4-chlorophenyl)tropane 2-carboxylate, hydrochloride, (1+1), white crystals, m.p. 295°–297° C.

(1R,2R,3S)-3-(4-Methylphenyl)tropane 2-carboxylate, hydrochloride, white crystals, m.p. 264°–266° C.

(1R,2R,3S)-3-(2-Naphthyl)tropane 2-carboxylate, hydrochloride, white crystals, m.p. 189°–210° C. (slowly decomposing).

(1R,2R,3S)-3-(3,4-Dichlorophenyl)tropane 2-carboxylate, hydrochloride, white crystals.

(1R,2R,3S)-3-(4-phenyl-phenyl)tropane 2-carboxylate, hydrochloride, white crystals.

(1R,2R,3S)-3-(4-t-Butyl-phenyl)tropane 2-carboxylate, hydrochloride, white crystals.

EXAMPLE 6

(1R,2R,3S)-2-(3-Methyl-1,2,4-oxadiazol-5-yl)-3-(4-fluorophenyl)tropane, hydrochloride.

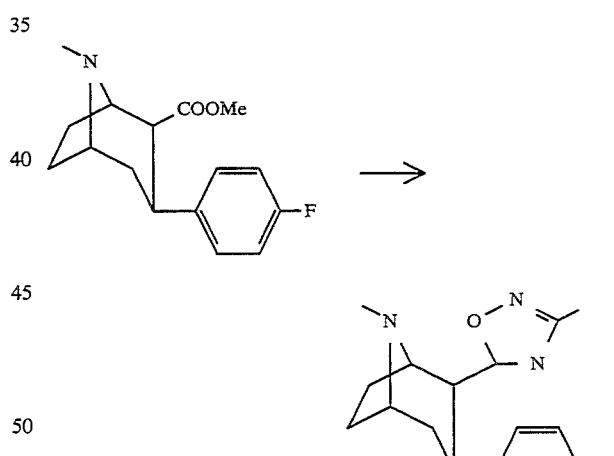

To a mixture of (1R,2R,3S)-2-carbomethoxy-3-(4-fluorophenyl)tropane, methyl amide oxime (0.37 g, 5 mmol) and pulverized molecular sieves (4 A, 2 g) in absolute ethanol (20 ml) was added sodium (0.15 g, 6.5 mmol) and the mixture was refluxed for 4 hours. The reaction mixture was filtered after cooling to ambient temperature and was concentrated in vacuo. The remanescens was dissolved in diethyl ether (30 ml) and the organic phase was washed 3 times with water. The organic phase was dried and a solution of hydrochloric acid in diethyl ether was added to precipitate the title compound as white crystals, m.p. approximately 100° C., hygroscopic when heated.

EXAMPLE 7

(1R,2S,3S )-2-(3-Methyl-1,2,4-oxadiazol-5-yl)-3-(4-fluorophenyl)tropane, hydrochloride.

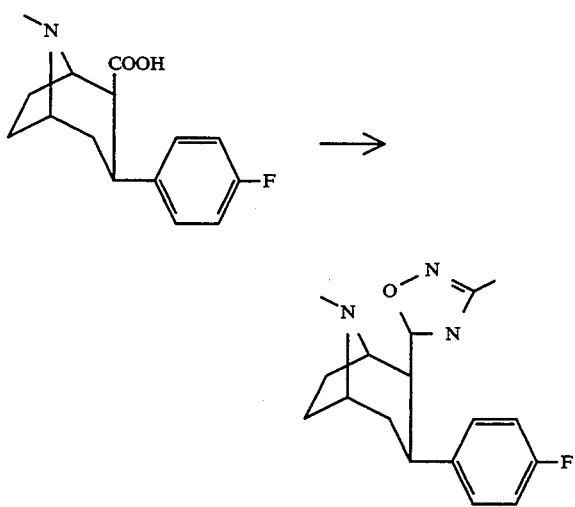

A solution of (1R,2S,3S)-3-(4-fluorophenyl)tropane 2-carboxylate (0.5 g, 1.25 mmol) in absolute tetrahydrofurane (10 ml) was heated to reflux and carbonyl diimidazole (0.4 g, 2.5 mmol) was added. The mixture was refluxed for one hour followed by addition of acetamide oxime (0.35 g, 4.7 mmol) and reflux for 16 hours. After cooling of the reaction mixture to ambient temperature, water (10 ml) was added and the mixture was extracted with diethyl ether. The organic phase was washed three times with water (10 ml), dried and after evaporation of the solvent in vacuo (1R,2S,3S)-2-(3-methyl-1,2,4-oxadiazol-5-yl)-3-(4-fluorophenyl)tropane was obtained as white crystals, m.p. 193°–195° C. The product was dissolved in a small amount of diethyl ether and the title compound precipitates as white crystals, m.p. <100° C. (hygroscopic) by addition of a solution of hydrochloric acid in diethyl ether.

The following compounds were made in a similar way by reaction of appropriate amide oximes with either ester or acid derivatives:

(1R,2R,3S)-2-(3-Phenyl-1,2,4-oxadiazol-5-yl)-3-benzyltropane, hydrochloride, white crystals, m.p. 186°–187° C.

(1R,2R,3S)-2-(3-Phenyl-1,2,4-oxadiazol-5-yl)-3-(4--chlorophenyl)-tropane, hydrochloride, white crystals, m.p. 289°–291° C.

(1R,2R,3S)-2-(3-Phenyl-1,2,4-oxadiazol-5-yl)-3-(4-chlorophenyl)-tropane+(1S ,2S,3R)-2-(3-phenyl-1,2,4oxadiazol-5-yl)-3-(4-chlorophenyl)-tropane (1+1), white crystals, m.p. 108°–109° C.

(1R,2R,3S)-2-(3-Phenyl-1,2,4-oxadiazol-5-yl)-3-(4-methylphenyl)-tropane, hydrochloride, white crystals, m.p. 283°–284° C.

(1R,2S,3S )-2-(3-Phenyl-1,2,4-oxadiazol-5-yl)-3-(4-fluorophenyl)tropane, hydrochloride, white crystals, m.p. 229°–230° C.

(1R,2R,3S)-2-(3-Phenyl-1,2,4-oxadiazol-5-yl)-3-(4-fluorophenyl)tropane, hydrochloride, white crystals, m.p. 267°–271° C.

(1R,2R,3S)-2-(3-Benzyl-1,2,4-oxadiazol-5-yl)-3-(4-fluorophenyl)tropane, hydrochloride, amorphous.

(1R,2R,3S)-2-(3-Cyclopropyl-1,2,4-oxadiazol-5-yl)-3-(4-fluorophenyl)tropane, hydrochloride, amorphous.

(1R,2R,3S)-2-(3-(4-Phenyl-phenyl)-1,2,4oxadiazol-5-yl)-3-(4-fluorophenyl) tropane, white crystals, m.p. 127°–128° C.

(1R,2R,3S)-2-(3-Phenyl-1,2,4-oxadiazol-5-yl)-3-(2-naphthyl)tropane, hydrochloride, amorphous.

(1R,2R,3S )-2-(3-Methyl-1,2,4-oxadiazol-5-yl)-3-(2-naphthyl)tropane, hydrochloride, white crystals, m.p. 245°–246° C.

(1R,2R,3S )-2-(3-Phenyl-1,2,4-oxadiazol-5-yl)-3-(3,4-dichlorophenyl)-tropane, hydrochloride, white amorphous substance, m.p. 60°–80° C.

(1R,2R,3S)-2-(3-(4-Chlorophenyl)-1,2,4-oxadiazol-5-yl)-3-(4-methylphenyl) -tropane, hydrochloride, white crystals, m.p. 273°–274° C.

(1R,2R,3S)-2-(3-(4-Fluorophenyl)-1,2,4-oxadiazol-5-yl)-3-(4-methylphenyl) -tropane, hydrochloride, white crystals, m.p. 281°–286° C.

(1R,2R,3S)-2-(3-Phenyl-1,2,4-oxadiazol-5-yl)-3-(4-phenyl-phenyl)tropane, hydrochloride, white crystals, m.p. 307°–309° C.

(1R,2R,3S)-2-(3-Methyl-1,2,4-oxadiazol-5-yl)-3-(4-phenyl-phenyl)tropane, hydrochloride, white crystals, m.p. 259°–261° C.

(1R,2R,3S)-2-(3-(2-thienyl)-1,2,4-oxadiazol-5-yl)-3-(4-methylphenyl)-tropane, hydrochloride, white crystals, m.p. 276°–278° C.

(1R,2R,3S )-2-(3-Methyl-1,2,4-oxadiazol-5-yl)-3-(3,4-dichlorophenyl)-tropane, hydrochloride, white crystals, m.p. 128°–130° C.

(1R,2S,3S )-2-(3-Phenyl-1,2,4-oxadiazol-5-yl)-3-(2-naphthyl)tropane, hydrochloride, amorphous.

(1R,2R,3S)-2-(3-Methyl-1,2,4-oxadiazol-5-yl)-3-benzyltropane, hydrochloride, white crystals, m.p. 179°–180° C.

(1R,2R,3S)-2-(3-(2-thienyl)-1,2,4-oxadiazol-5-yl)-3-(3, 4-dichlorophenyl) -tropane, hydrochloride, white crystals, m.p. 228°–230° C.

(1R,2R,3S)-2-(3-Methyl-1,2,4-oxadiazol-5-yl)-3-(4-chlorophenyl)-tropane, hydrochloride, white crystals, m.p. 143°–145° C.

(1R,2R,3S)-2-(3-(2-Thienyl)-1,2,4-oxadiazol-5-yl)-3-(2-naphthyl)tropane, hydrochloride, white amorphous substance.

(1R,2R,3S)-2-(3-Methyl-1,2,4-oxadiazol-5-yl)-3-(4-t-butylphenyl)-tropane, hydrochloride, white crystals, m.p. 290°–291° C.

(1R,2R,3S )-2-(3-(4-Pyridyl)-1,2,4-oxadiazol-5-yl)-3-(3,4-dichlorophenyl) -tropane, dihydrochloride, white crystals (hygroscopic), m.p. (base) 174°–184° C.

(1R,2R,3S840 )-2-(3-(4-Pyridyl)-1,2,4-oxadiazol-5-yl)-3-(3,4-dichlorophenyl) -tropane, dihydrochloride, white crystals (hygroscopic), m.p. (base) 174°–184° C.

(1R,2R,3S)-2-(3-(2-Pyridyl)-1,2,4-oxadiazol-5-yl)-3-(3,4-dichlorophenyl) -tropane, dihydrochloride, white crystals (hygroscopic), m.p. (base) 155°–162° C.

(1R,2R,3S)-2-(3-(4-Pyridyl)-1,2,4-oxadiazol-5-yl)-3-(4-chlorophenyl)-tropane, dihydrochloride, white crystals, m.p. 170°–175° C.

(1R,2R,3S)-2-(3-(3-Pyridyl)-1,2,4-oxadiazol-5-yl)-3-(4-chlorophenyl)-tropane, dihydrochloride, white crystals (hygroscopic).

(1R,2R,3S)-2-(3-(2-Pyridyl)-1,2,4-oxadiazol-5-yl)-3-(4-chlorophenyl)-tropane, dihydrochloride, white crystals (hygroscopic), m.p. (base) 163°–165° C.

EXAMPLE 8

(1R,2R,3S)-2-(3-(4-Pyridyl)-1,2,4-oxadiazol-5-yl)-3-(3,4-methylenedioxyphenyl) tropane.

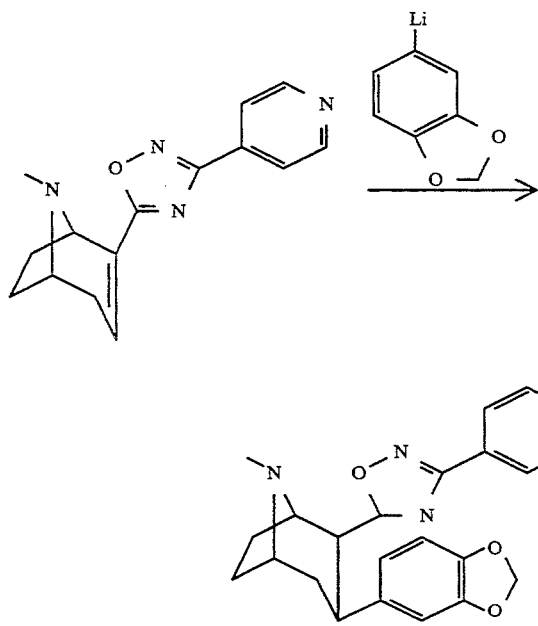

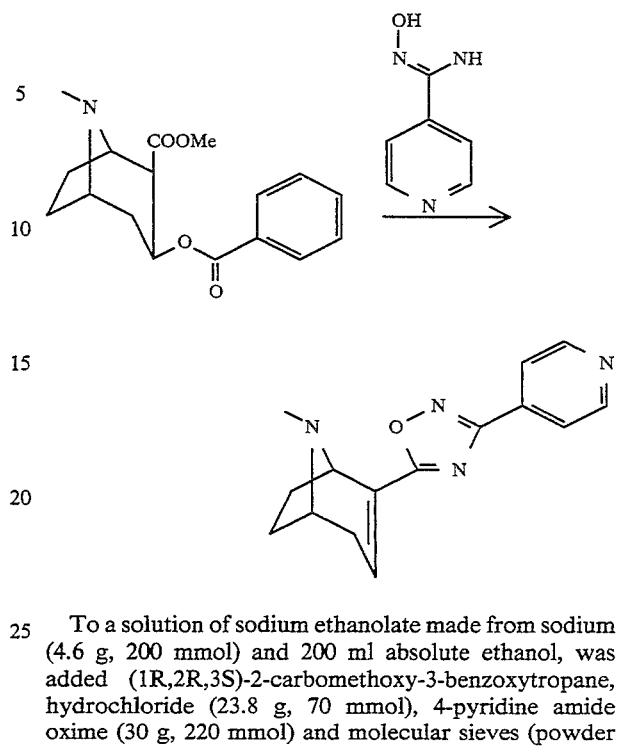

A solution of 4-brom-1,2-methylenedioxybenzene (4 g, 20 mmol) in 25 ml absolute tetrahydrofurane was cooled to −78° C. and n-butyllithium (2.5M, 8 ml, 20 mmol) was added over five minutes yielding a suspension. The mixture was stirred for 30 minutes and a solution of (1R)-2-(4-pyridyl)-1,2,4-oxadiazol-5-yl)anhydroecgonine (2 g, 7.5 mmol) in 20 ml absolute tetrahydrofurane was added over 15 minutes yielding a violet reaction mixture. After another 15 minutes stirring the reaction mixture was quenched by addition of trifluoroacetic acid (1.6 ml, 20.5 mmol) and the mixture was allowed to reach room temperature. 25 ml Water was added and the pH was adjusted to 1 by addition of concentrated hydrochloric acid. The aquoues phase was washed twice with diethyl ether and the pH was adjusted to 10 by addition of 25% ammonium hydroxide. The alkaline water phase was extracted twice with methylene chloride and the combined methylene chloride phases were concentrated in vacuo yielding a mixture of the (1R,2R,3S) and (1R,2S,3S) isomers. This mixture was dissolved in 15 ml methanol and 10 ml sodium methanolate in methanol was added and the mixture was heated at reflux over night. The mixture was concentrated in vacuo and was dissolved in diethyl ether and was washed 3 times with water. The ether phase was concentrated in vacuo and the crude product was subjected to column chromatography using methylene chloride+acetone+methanol (4+1+1) as eluent. The fractions containing the product were concentrated in vacuo and the product was recrystallized from n-heptane yielding the title compound as white crystals, m.p. 110°-112° C.

EXAMPLE 9

(1R)-2-(4-Pyridyl)-1,2,4-oxadiazol-5-yl)-anhydroecgonine.

To a solution of sodium ethanolate made from sodium (4.6 g, 200 mmol) and 200 ml absolute ethanol, was added (1R,2R,3S)-2-carbomethoxy-3-benzoxytropane, hydrochloride (23.8 g, 70 mmol), 4-pyridine amide oxime (30 g, 220 mmol) and molecular sieves (powder 1.5 g) and the mixture was heated at reflux over night. Water (500 ml) was added and the suspension was extracted twice with diethylether. The ether phase was washed with water and was extracted with 2M hydrochloric acid (150 ml). The pH of the acidic water extract was adjusted to ten by addition of a 50% sodium hydroxide solution and the mixture was extracted twice with diethyl ether. The ether extracts were dryed and concentrated in vacuo yielding an oil which solidifyes upon standing and was recrysttalized from water+ethanol (1+1) yielding the title compound as off white crystals, m.p. 104°-105° C.

EXAMPLE 10

Benzyl amide oxime.

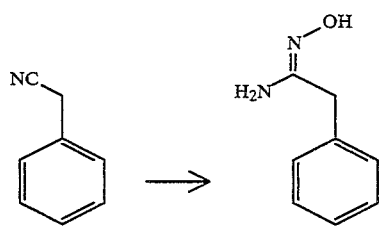

To a solution of hydroxyl ammoniumchloride (38.2 g, 550 mmol) in absolute methanol (300 ml), at room temperature, was added a methanolic solution of sodium methanolate made by reaction of sodium (13 g, 565 mmol) with absolute methanol (200 ml). The precipitate of sodium chloride was removed by filtration and benzyl cyanide (57.7 ml, 500 mmol) was added. The reaction mixture was stirred for 16 hours at room temperature and was then concentrated in vacuo. The remanescens was triturated with cold methylene chloride, filtered and the crystals were washed with ice cold methylene chloride yielding the title compound as white crystals, m.p. 120°-125° C.

The following compounds were made in a similar way:

4-Phenyl-phenyl amide oxime, white crystals, m.p. 177°–178° C..

Cyclopropyl amide oxime, purification by column chromatography first using ethyl acetate then ethyl acetate+methanol (10%) as eluent, white crystals, m.p. 38°–40° C.

Phenyl amide oxime, white crystals, m.p. 76°–77° C.

4-Chlorophenyl amide oxime, white crystals, m.p. 113°–115° C.

4-Fluorophenyl amide oxime, white crystals, m.p. 66°–67° C.

2-Thienyl amide oxime, white crystals, decomp. 200° C.

4-Pyridine amide oxime, white crystals.
3-Pyridine amide oxime, white crystals.
2-Pyridine amide oxime, white crystals.

EXAMPLE 11

(1R,2R,3S)-N-Normethyl-2-(3-phenyl-1,2,4-oxadiazol-5-yl)-3-(4-chlorophenyl)-tropane, hydrochloride.

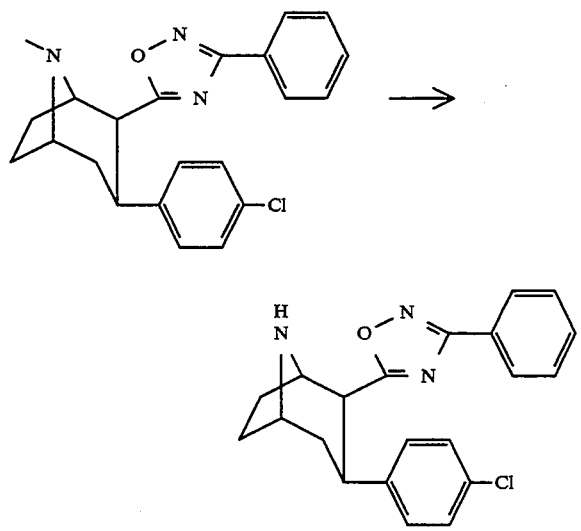

A mixture of (1R,2R,3S)-2-(3-phenyl-1,2,4-oxadiazol-5-yl)-3-(4-chlorophenyl)-tropane (3 g, 8 mmol) and 2,2,2-trichloroethyl chloroformate (5 ml, 36 mmol) in dry toluen (50 ml) was refluxed for 2 hours. The reaction mixture was concentrated in vacuo and to the remanescens was added methylene chloride which subsequently was washed with water. The organic phase was dried and concentrated in vacuo. The remanescens was dissolved in 50% aqueous acetic acid (75 ml) and zinc dust (1 g) was added to the reaction mixture which thereafter was stirred at ambient temperature for 16 hours. Concentrated ammonium hydroxide was added to basic reaction and the mixture was extracted twice with diethyl ether. The combined organic phase was dried and concentrated in vacuo and the crude reaction product was purified by column chromatography using methylene chloride, methanol, acetone (4+1+1) as eluent. (1R,2R,3S)-N-normethyl-2-(3-phenyl-1,2,4-oxadiazol-5-yl)-3-(4-chlorophenyl)-tropane was obtained as white crystals, m.p. 185°–187° C. which were dissolved in a small amount of ethanol and by addition of a solution of hydrochloric acid in diethyl ether the title compound precipitates as white crystals (hygroscopic), m.p. <100° C.

The following compound was made in a similar way:
(1R,2R,3S )-N-Normethyl-2-(3-phenyl-1,2,4-oxadiazol-5-yl)-3-(3,4-dichlorophen yl)-tropane, hydrochloride, white crystals (hygroscopic), m.p. 100°–150° C.

EXAMPLE 12

(1R,2R,3S)-N-Normethyl-N-allyl-2-(3-phenyl-1,2,4-oxadiazol-5-yl)-3-(4-chlorophenyl)-tropane, hydrochloride.

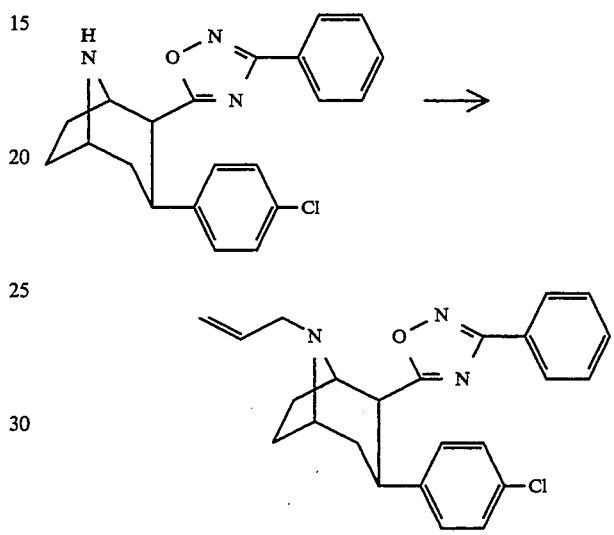

A mixture of (1R,2R,3S)-N-normethyl-2-(3-phenyl-1,2,4-oxadiazol-5-yl)-3-(4-chlorophenyl)-tropane (0.29 g, 0.8 mmol), 3-bromo-1-propene (0.1 ml, 1 mmol) and potassium carbonate (0.14 g, 1 mmol) in absolute ethanol (25 ml) was refluxed for 3 hours. The product was taken up in diethyl ether and the organic phase was washed twice with water, dried and concentrated in vacuo. The crude product was dissolved in a small amount of diethyl ether and by addition of a solution of hydrochloric acid in diethyl ether the title compound precipitates as white crystals, m.p. 259°–260° C.

The following compounds were made in a similar way:

(1R,2R,3S)-N-Normethyl-N-(2-hydroxyethyl)-2-(3-phenyl- 1,2,4-oxadiazol-5-yl)-3-(4-chlorophenyl)-tropane, hydrochloride, white crystals, m.p. 266°–268° C.

(1R,2R,3S)-N-Normethyl-N-ethyl-2-(3-phenyl-1,2,4-oxadiazol-5-yl)-3-(4-chlorophenyl) -tropane, hydrochloride, white crystals, m.p. 309°–310° C.

(1R,2R,3S)-N-Normethyl-N-benzyl-2-(3-phenyl-1,2,4-oxadiazol-5-yl)-3-(4-chlorophenyl) -tropane, hydrochloride, white crystals, m.p. 241°–246° C.

(1R,2R,3S)-N-Normethyl-N-propargyl-2-(3-phenyl-1,2,4-oxadiazol-5-yl)-3-(4-chlorophenyl )-tropane, hydrochloride, off white amorphous.

(1R,2R,3S)-N-Normethyl-N-cyclopropylmethyl-2-(3-phenyl-1,2,4-oxadiazol-5-yl)-3-(4-chlorophenyl)-tropane, hydrochloride, white crystals, m.p. 245°–248° C.

EXAMPLE 13

(1R,2R,3S)-N-Normethyl-N-(2-acetoxyethyl)-2-(3-phenyl-1,2,4-oxadiazol-5-yl)-3-(4-chlorophenyl)-tropane, hydrochloride.

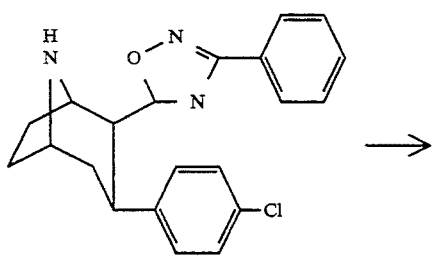

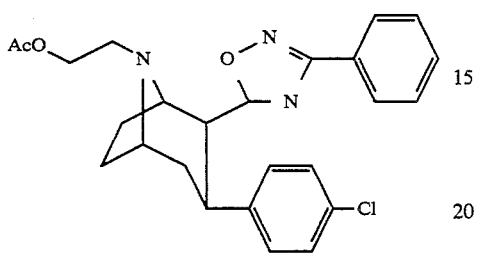

To a solution of (1R,2R,3S)-N-normethyl-2-(3-phenyl-1,2,4-oxadiazol-5-yl)-3-(4-chlorophenyl)-tropane (0.48 g, 1.3 mmol) in absolute dimethylformamide (4 ml) at room temperature was added sodium hydride (40 mg, 80%, 1.3 mmol) and the mixture was stirred for 20 minutes. 2-Bromoethyl acetate (150 µl, 1.3 mmol) was added and the reaction mixture was stirred over night at 70° C. After cooling to ambient temperature was ice added and the mixture was extracted with ethyl acetate. The organic phases was concentrated in vacuo and the crude product was subjected to column chromatography using ethylacetate+10% methanol as eluent. The fractions containing the product was concentrated in vacuo yielding an brown oil, which was dissolved in diethyl ether and added hydrochloric acid in diethyl ether to precipate the title comppound as white crystals, m.p. 245°-248° C.

EXAMPLE 14

(1R,2S,3S)-2-Hydroxymethyl-3-(4-fluorophenyl)tropane.

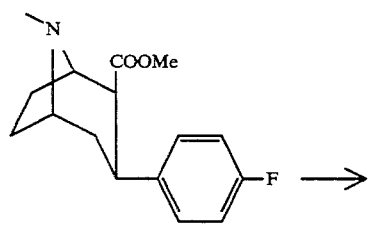

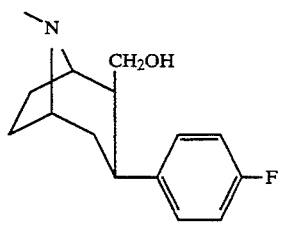

To a suspension of lithium aluminum hydride (0.8 g, 21 mmol) in diethyl ether (30 ml), at room temperature, was slowly added a solution of (1R,2S,3S)-2-carbomethoxy-3-(4-fluorophenyl)tropane (5 g, 18 mmol) in 100 ml diethyl ether. The reaction completes after stirring for 10 minutes and was quenched by addition of 0.8 ml water, 0.8 ml sodium hydroxide (15%) and 2 ml water. The aluminum salts were removed by filtration and the solvent was removed in vacuo leaving an oil. The title compound precipitates upon trituration with pentane as white crystals, m.p. 79°-80° C.

The following compound was made in a similar way:

(1R,2R,3S)-2-Hydroxymethyl-3-(4-fluorophenyl)tropane, white crystals, m.p. 169°-170° C.

EXAMPLE 15

(1R,2R,3S)-2-(4-Chlorophenoxy-methyl)-3-(4-fluorophenyl)tropane, hydrochloride.

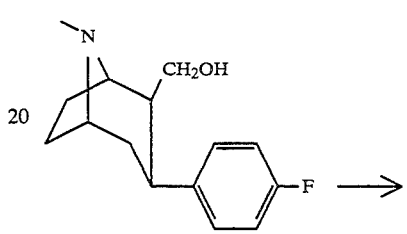

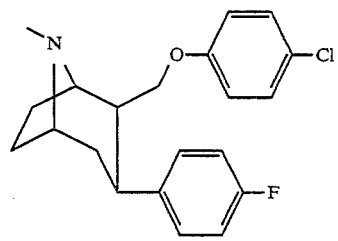

A mixture of (1R,2R,3S)-2-hydroxymethyl-3-(4-fluorophenyl)tropane (1.8 g, 7.2 mmol), p-toluen-sulphonylchloride (2 g, 10.5 mmol) and triethyl amine (1.6 ml, 12 mmol) in methylene chloride (50 ml) was stirred at room temperature for 20 hours and the reaction mixture was concentrated in vacuo. Water (50 ml) and diethyl ether (50 ml) was added and the mixture was stirred for ½ hour. The organic phase was washed once with sodium hydroxide (1M), twice with water, and was then dried and concentrated in vacuo. The remanescens was dissolved in a small amount of absolute ethanol and was, at room temperature, added to a solution of sodium 4-chloro-phenolate in absolute ethanol, made by addition of sodium (0.24 g, 10 mmol) to a solution of p-chlorophenol in absolute ethanol. The mixture was refluxed for three days and was concentrated in vacuo. The remanescens was stirred in a mixture of water and diethyl ether and the organic phase was washed with water. After drying and concentration in vacuo, the crude product was subjected to column chromatography first with ethyl acetate and later with ethyl acetate and methanol (10%) as eluent. An oil was isolated which was dissolved in a small amount of diethyl ether and the title compound was precipitated, by addition of hydrochloric acid in diethyl ether, as white crystals (hygroscopic), m.p. 70°-75° C.

The following compounds were made in a similar way:

(1R,2R,3S)-2-(4-Chlorophenoxy-methyl)-3-(3,4-dichlorophenyl)tropane, hydrochloride, white crystals (hygroscopic), m.p. 45°-50° C.

(1R,2R,3S)-2-(4-Chlorophenoxy-methyl)-3-(4-methylphenyl)tropane, hydrochloride, white crystals (hygroscopic), m.p. 65°–70° C.

EXAMPLE 16

(1R,2S,3S)-2-(4-Benzoyloxy-methyl)-3-(4-fluorophenyl)tropane, hydrochloride.

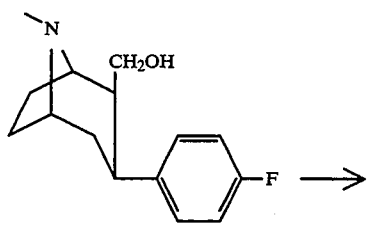

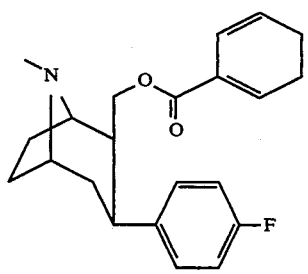

To a mixture of (1R,2S,3S)-2-hydroxymethyl-3-(4-fluorophenyl)tropane (0.5 g, 2 mmol) and potassium carbonate (0.35 g, 2.5 mmol) in tetrahydrofurane (25 ml), at room temperature, was slowly added a solution of benzoyl chloride (0.3 ml, 2.5 mmol) in tetrahydrofurane (5 ml). The reaction mixture was stirred for to hours at ambient temperature and was concentrated in vacuo. Water (20 ml) was added and the suspension was extracted twice with diethyl ether. The organic phase was dried and was concentrated in vacuo. Thereafter the crude product was dissolved in a small amount of diethyl ether and the title compound was precipitated, by addition of hydrochloric acid in diethyl ether, as white crystals, m.p. 230°–233° C.

The following compound was made in a similar way:
(1R,2R,3S)-2-(4-Benzoyloxy-methyl)-3-(4-fluorophenyl)tropane, hydrochloride, white crystals, m.p. 90°–91° C.

EXAMPLE 17

(1R,2R,3S)-3-(4-Fluorophenyl)tropane 2-carboxamide, hydrochloride.

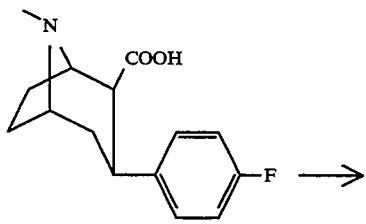

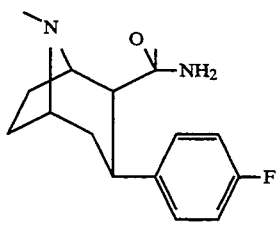

A mixture of (1R,2R,3S)-3-(4-fluorophenyl)tropane 2-carboxylate (3.4 g, 12.5 mmol) and thionyl chloride (10 ml) was refluxed for one hour and the reaction mixture was concentrated in vacuo. The remanescens was ice cooled and a solution of ammonium hydroxide (25%, 20 ml) was slowly added. The mixture was stirred at room temperature for one hour and the water was decanted from the formed oil. The crude product was dissolved in a small amount of ethanol and concentrated hydrochloric acid (2 ml) was added. Addition of diethyl ether precipitates the title compound which was recrystallized from isopropanol yielding white crystals, m.p. 258°–260° C.

The following compound was made in a similar way:
(1R,2R,3S)-3-(3,4-Dichlorophenyl)tropane 2-carboxamide, white crystals, m.p. 168°–170° C.

EXAMPLE 18

(1R,2R,3S)-3-(3,4-Dichlorophenyl)tropane 2-cyanide, hydrochloride, white crystals.

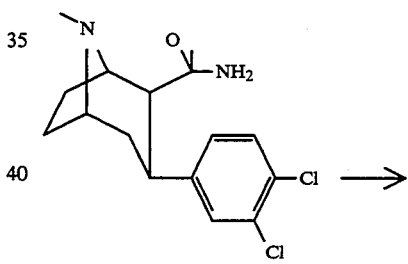

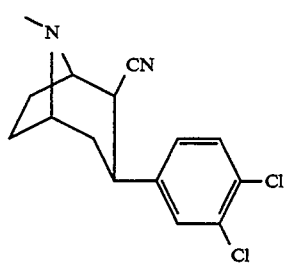

To an icecooled solution of triphenylphosphine (2.2 g, 8.5 mmol) in 50 ml methylenechloride was added bromine (0.43 ml, 8.5 mmol) yielding a slightly brown solution. The brown color was removed by addition of a small amount of triphenylphosphine. To the icecooled solution was added (1R,2R,3S)-3-(3,4-dichlorophenyl)-tropane 2-carboxamide (2.1 g, 6.7 mmol) and triethylamine (2.4 ml, 17 mmol) and the reaction mixture was stirred for 15 minutes. The reaction mixture was washed with water, dryed and concentrated in vacuo. The remanescens was extracted with diethyl ether and a crude product was precipitated by addition of hydrochloric acid in diethyl ether. The crude product was recrystallized from ethanol yielding the title compound as white crystals, m.p. 268°-270° C.

EXAMPLE 19

(1R,2R,3S)-2-(4-Chlorophenoxy)carbonyl-3-(4-fluorophenyl)tropane.

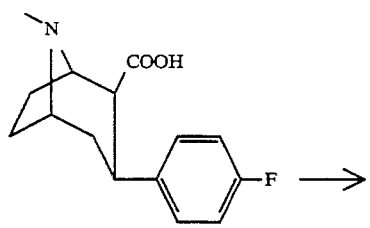

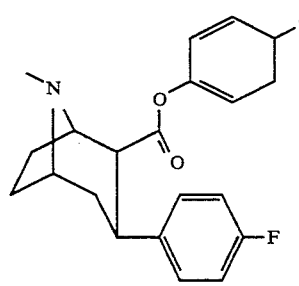

A mixture of (1R,2R,3S)-3-(4-fluorophenyl)tropane 2-carboxylate (1.4 g, 5 mmol) and thionyl chloride (5 ml) was refluxed for one hour and the reaction mixture was concentrated in vacuo. The remanescens was suspended in diethyl ether (20 ml) and a solution of 4-chlorophenol (0.64 g, 5 mmol) and triethyl amine (1.4 ml, 10 mmol) in diethyl ether (10 ml) was added at room temperature. The mixture was stirred at room temperature over night and tetrahydrofurane (30 ml) was added and the mixture was refluxed for three hours. The reaction was quenched by addition of water (50 ml) and was extracted with diethyl ether. The combined organic phase was washed with sodium hydroxide (1M) and three times with water. After drying and concentration in vacuo the crude product was subjected to column chromatography first with ethyl acetate and later with ethyl acetate and methanol (20%) as eluent yielding the title compound as white crystals, m.p. 64°-66° C.

EXAMPLE 20

(1RS,2RS)-2-Carbomethoxy-3-tropanone.

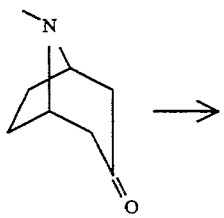

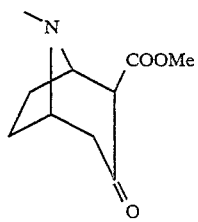

To a suspension of sodium hydride (3.2 g 80%, 107 mmol, prewashed in cyclohexane) and dimethylcarbonate (9.13 ml, 108 mmol) in absolute cyclohexane heated to reflux temperature, a solution of (+ —)-3-tropanone (6.9 g, 50 mmol) in 50 ml absolute cyclohexane was added over 15 minutes. No hydrogen evolution was apparent so 0.2 ml methanol was added. The reaction mixture was stirred over night at reflux temperature and after cooling to ambient temperature 75 ml water was carefully added. To the water phase was added 40 g ammonium chloride and the resulting mixture was extracted 8 times with methylene chloride. The combined methylene chloride organic phases were dried and concentrated in vacuo followed by column chromatography of the crude product using methylene chloride with increasing amounts (up to 10%) of methanol as eluent. The fractions containing the product were concentrated in vacuo and the resulting oil was subjected to kugelrohr destillation (1 mbar, 120° C., yielding the title compound as orange crystals, m.p. 104°-107° C.

EXAMPLE 21

(1RS,2RS,3RS)-2-Carbomethoxy-3-hydroxy-tropane, hydrochloride.

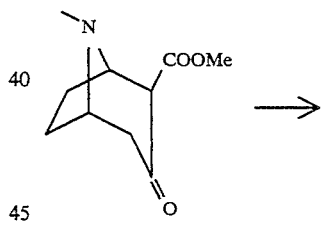

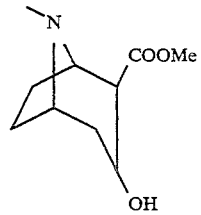

To a solution of (1RS,2RS)-2-carbomethoxy-3-tropanone (17 g, 85 mmol) in 750 ml methanol cooled to −35° C. was added sodium borohydride (17 g, 450 mmol) and the mixture was stirred for 4 hours. The cooled solution was quenched by slow addition of concentrated hydrochloric acid (40 ml) and the mixture was concentrated in vacuo. Water (400 ml) was added and the pH was adjusted to 3 by addition of concentrated hydrochloric acid. After having washed the water phase three times with diethyl ether pH was adjusted to 11 by addition of concentrated ammonium hydroxide and the water phase was extracted three times with methylene chloride. Concentration in vacuo yields an oil which was dissolved in ethanol and added cocncentrated hydrochloric acid followed by concentration in vacuo. Freeze drying the residue yielded the title compound as an amorphous product.

EXAMPLE 22

(1RS)-Anhydroecgonine methyl ester.

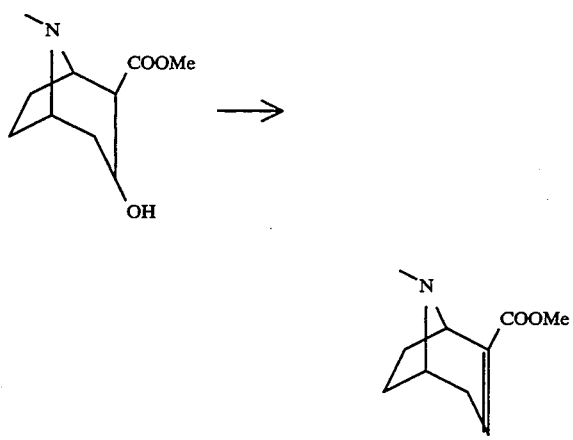

A mixture of (1RS,2RS,3RS)-2-carbomethoxy-3-hydroxy-tropane, hydrochloride (0.5 g, 2.1 mmol) and thionyl chloride (0.4 ml, 5.3 mmol) was stirred at 60° C. for two hours resulting in a clear solution. After cooling to ambient temperature crushed ice was added and pH was adjusted to 11 by addition of concentrated ammonium hydroxide. The mixture was extracted twice with methylene chloride and the solvent was removed in vacuo yielding the title compound as an oil which was destilled, 1 mbar 70°–85° C.

EXAMPLE 23

(1R,2S,3S)-2-(4'-Fluoro-benzoyl)-3-(4-fluorophenyl)-tropane and (1R,2R,3S)-2-(4'-fluoro-benzoyl-3-(4-fluorophenyl)tropane.

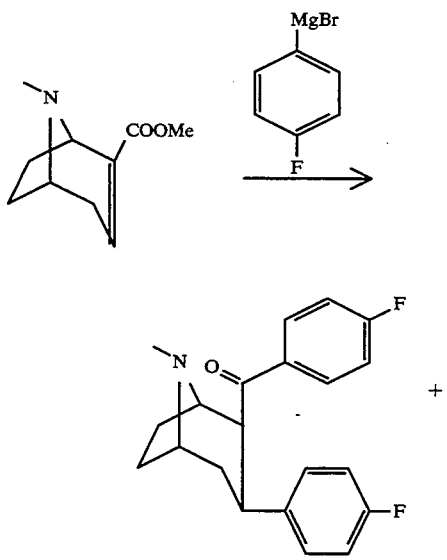

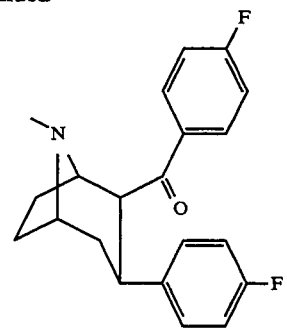

Grignard reagent was made in a three necked reaction flask equipped with mechanical stirring, an intensive condenser and a pressure equilibrated funnel, using 4-bromo-fluorobenzene (55 ml, 500 mmol) and magnesium turnings (12.6 g, 520 mmol) in 500 ml absolute diethyl ether. The solution of grignard reagent was cooled to −20° C. and a solution of (−)-anhydroecgonine methyl ester (43 g, 233 mmol) in 200 ml absolute diethyl ether was added over ½ hour. The reaction was first stirred one hour at −20° C. and then 16 hours at room temperature and was finally quenched by addition of water (50 ml). The mixture was acidified by addition of hydrochloric acid (4M, 50 ml) and the aqueous phase was washed twice with diethyl ether. To the aqueous phase was added ammonium hydroxide (25%) to basic reaction and the resulting mixture was finally extracted three times with diethyl ether. After drying and concentration of the combined organic phase in vacuo, the crude product was subjected to column chromatography using diethyl ether+triethyl amine (5%) as eluent, yielding (1R,2S,3S)-2-(4'-fluoro-benzoyl)-3-(4-fluorophenyl)tropane, white crystals m.p. 178°–180° C. and (1R,2R,3S)-2-(4'-fluoro-benzoyl)-3-(4-fluorophenyl)tropane, white crystals m.p. 124°–140° C.

EXAMPLE 24

(1R,2R,3S)-3-(3,4-Dichlorophenyl)-2-methylcyanotropane, hydrochloride.

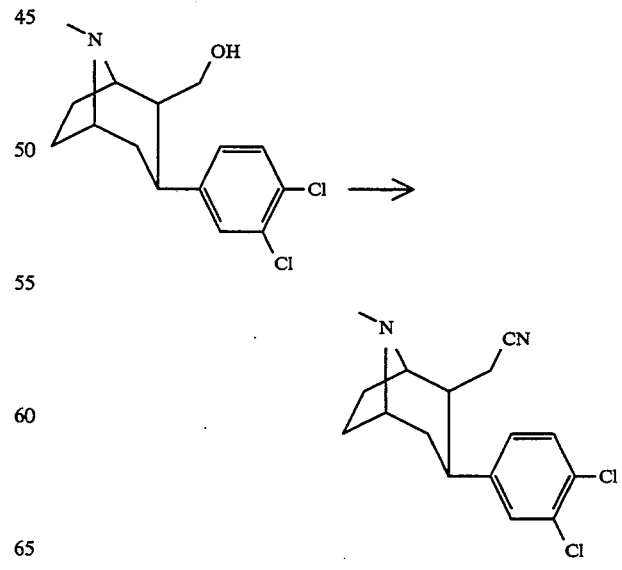

A solution of (1R,2S,3S)-2-hydroxymethyl-3-(3,4-dichloro-phenyl)tropane (6.9 g, 23 mmol), triethyl amine (7 ml, 51 mmol) and p-toluenesulphonyl chloride (6.4 g, 34 mmol) in 50 ml methylene chloride was stirred over night at room temperature followed by concentration of the reaction mixture in vacuo. Water (50 ml) and diethylether (50 ml) was added and the mixture was stirred at room temperature for 30 minutes. The ether phase was first washed once with 15 ml 1M sodium hydroxide solution followed by three times water and was finally concentrated in vacuo. The residue was dissolved in ethanol (200 ml) and sodium cyanide-(2.5 g, 51 mmol) was added. The mixture was stirred at reflux temperature for two days followed by concentration in vacuo. The residue was stirred with diethyl ether and water and the ether phase was washed twice with water and concentrated in vacuo. The crude product was subjected to column chromatography using methylene chloride+acetone+methanol (4+1+1) as eluent and the fractions containing the product was concentrated in vacuo. The product was dissolved in a small amount of methylene chloride and a solution of hydrochloric acid in diethylether (2M) was added. The mixture was concentrated in vacuo yielding the title compound as a hydroscopic crystals.

EXAMPLE 25

(1R,2R,3S)-2-(3-Phenyl-1,3, 4-oxadiazol-5-yl)-3-(4-chlorophenyl)-tropane

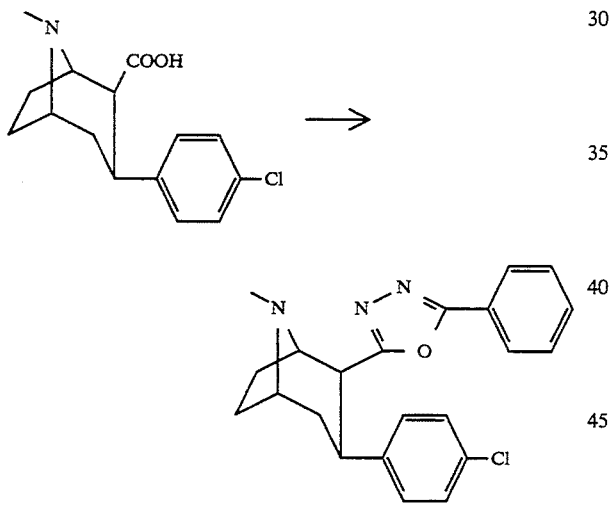

To a suspension of (1R,2R,3S)-3-(4-chlorophenyl)tropane 2-carboxylate, hydrochloride (1 g, 3.2 mmol) in 20 ml absolute tetrahydrofurane at 60° C., N,N-carbonyldiimidazole (0.65 g, 4 mmol) was added. After stirring for 15 minutes a clear solution was obtained and benzhydrazide (0.54 g, 4 mmol) was added. The reaction was stirred over night at 60° C. and was concentrated in vacuo. The residue was stirred with 1M sodium hydroxide solution (10 ml) and diethyl ether (50 ml) and the ether phase was concentrated in vacuo. The residue was added phosphorous oxychloride (2 ml) and the mixture was stirred at 60° C. for two hours. The reaction mixture was cooled on an icebath and crushed ice was added followed by a 10M sodium hydroxide solution until alkaline pH. The water phase was extracted with ethyl acetate and the organic phase was concentrated in vacuo. The crude product was recrystalized from a mixture of ethanol and water yielding the title compound as white crystals, m.p. 164°–166° C.

The following compound was made in a similar way:
(1R,2R,3S)-2-(3-Phenyl-1,3,4-oxadiazol-5-yl)-3-(3,4-dichlorophenyl)-tropane, white crystals, m.p. 173°–174° C.

We claim:

1. A method of treating a disorder or disease of a living animal body, including a human, which disorder or disease is responsive to the inhibition of dopamine reuptake, comprising the step of administering to such a living animal body, including a human, in need thereof an effective amount of a compound having the formula

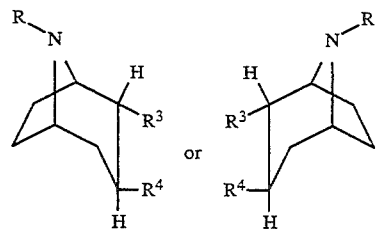

any mixture thereof, or a pharmaceutically-acceptable salt thereof; wherein

R is hydrogen, $C_{1-6}$-alkyl, $C_{2-6}$-alkenyl, $C_{2-6}$-alkenyl, $C_{2-6}$-alkynyl, $C_{3-7}$-cycloalkyl-$C_{1-6}$-alkyl or 2-hydroxyethyl;

$R^3$ is 1,2,4-oxadiazol-3-yl which may be substituted in the 5-position with phenyl which may be substituted one or two times with a substituent selected from the group consisting of halogen, $CF_3$, CN, $C_{1-6}$-alkoxy, $C_{1-6}$-alkyl, $C_{2-6}$-alkenyl, $C_{2-6}$-alkynyl, amino, or nitro; phenylphenyl; or benzyl which may be substituted one or two times with a substituent selected from the group consisting of halogen, $CF_3$, CN, $C_{1-6}$-alkoxy, $C_{1-6}$-alkyl, $C_{2-6}$-alkenyl, $C_{2-6}$-alkynyl, amino, or nitro; or 1,2,4-oxadiazol-5-yl which may by substituted in the 3-position with phenyl which may be substituted one or two times with a substituent selected from the group consisting of halogen, $CF_3$, CN, $C_{1-6}$-alkoxy, $C_{1-6}$-alkyl, $C_{2-6}$-alkenyl, $C_{2-6}$-alkynyl, amino, or nitro; phenylphenyl; or benzyl which may be substituted one or two times with a substituent selected from the group consisting of halogen, $CF_3$, CN, $C_{1-6}$-alkoxy, $C_{1-6}$-alkyl, $C_{2-6}$-alkenyl, $C_{2-6}$-alkynyl, amino, or nitro; and $R^4$ is phenyl which may be substituted one or two times with a substituent selected from the group consisting of halogen, $CF_3$, CN, $C_{1-6}$-alkoxy, $C_{1-6}$-alkyl, $C_{2-6}$-alkenyl, $C_{2-6}$-alkynyl, amino, nitro, or phenyl;

3,4-methylenedioxyphenyl;

benzyl which may be substituted one or two times with a substituent selected from the group consisting of halogen, $CF_3$, CN, $C_{1-6}$-alkoxy, $C_{1-6}$-alkyl, $C_{2-6}$alkenyl, $C_{2-6}$alkynyl, amino, or nitro; or naphthyl which may be substituted one or two times with a substituent selected from the group consisting of halogen, $CF_3$, CN, $C_{1-6}$-alkoxy, $C_{1-6}$-alkyl, $C_{2-6}$-alkenyl, $C_{2-6}$-alkynyl, amino, or nitro.

2. The method of claim 1, wherein depression or Parkinsonism is treated.

3. The method of claim 1, wherein drug addiction and/or abuse is treated.

4. The method of claim 3, wherein cocaine and/or amphetamine addiction and/or abuse is treated.

5. The method of claim 1, wherein the compound employed is (1R,2R,3S)-2-(3-Phenyl-1,2,4-oxadiazol-5-yl)-3-(4-fluorophenyl)tropane, (1R,2R,3S)-2-(3-Phenyl-1,2,4-oxadiazol-5-yl)-3-(4-methylphenyl)-tropane, (1R,2R,3S)-2-(3-Benzyl-1,2,4-oxadiazol-5-yl)-3-(4-fluorophenyl)tropane, (1R,2R,3S)-2-(3-(4-Phenyl-phenyl)-1,2,4-oxadiazol-5-yl)-3-(4-fluorophenyl)tropane, or (1R,2R,3S)-2-(3-Phenyl-1,2,4-oxadiazol-5-yl)-3-(2-naphthyl)tropane, or or a pharmaceutically-acceptable addition salt thereof.

6. The method of claim 1, wherein the active ingredient is administered in the form of a pharmaceutical composition thereof, in which it is present together with at least one pharmaceutically-acceptable carrier or diluent.

7. A compound having the formula

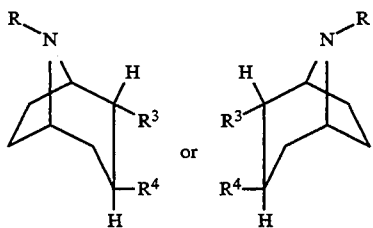

any mixture thereof, or a pharmaceutically-acceptable salt thereof; wherein

R is hydrogen, $C_{1-6}$-alkyl, $C_{2-6}$-alkenyl, $C_{2-6}$-alkynyl, $C_{3-7}$-cycloalkyl-$C_{1-6}$-alkyl or 2-hydroxyethyl;

$R^3$ is 1,2,4-oxadiazol-3-yl which may be substituted in the 5-position with phenyl which may be substituted one or two times with a substituent selected from the group consisting of halogen, $CF_3$, CN, $C_{1-6}$-alkoxy, $C_{1-6}$-alkyl, $C_{2-6}$-alkenyl, $C_{2-6}$-alkynyl, amino, or nitro; phenylphenyl; or benzyl which may be substituted one or two times with a substituent selected from the group consisting of halogen, $CF_3$, CN, $C_{1-6}$-alkoxy, $C_{1-6}$-alkyl, $C_{2-}$-alkenyl, $C_{2-6}$-alkynyl, amino, or nitro; or 1,2,4-oxadiazol-5-yl which may be substituted in the 3-position with phenyl which may be substituted one or two times with a substituent selected from the group consisting of halogen, $CF_3$, CN, $C_{1-6}$-alkoxy, $C_{1-6}$-alkyl, $C_{2-6}$-alkenyl, $C_{2-6}$-alkynyl, amino, or nitro; phenylphenyl; or benzyl which may be substituted one or two times with a substituent selected from the group consisting of halogen, $CF_3$, CN, $C_{1-}$-alkoxy, $C_{1-6}$-alkyl, $C_{2-6}$-alkenyl, $C_{2-6}$-alkynyl, amino, or nitro; and $R^4$ is phenyl which may be substituted one or two times with a substituent selected from the group consisting of halogen, $CF_3$, CN, $C_{1-6}$-alkoxy, $C_{1-6}$-alkyl, $C_{2-6}$-alkenyl, $C_{2-6}$-alkynyl, amino, nitro, or phenyl;

3,4-methylenedioxyphenyl;

benzyl which may be substituted one or two times with a substituent selected from the group consisting of halogen, $CF_3$, CN, $C_{1-6}$-alkoxy, $C_{1-6}$-alkyl, $C_{2-6}$-alkenyl, $C_{2-6}$-alkynyl, amino, or nitro; or naphthyl which may be substituted one or two times with a substituent selected from the group consisting of halogen, $CF_3$, CN, $C_{1-6}$-alkoxy, $C_{1-6}$-alkyl, $C_{2-6}$-alkenyl, $C_{2-6}$-alkynyl, amino, or nitro.

8. A compound of claim 7 which is (1R,2R,3S)-2-(3-Phenyl-1,2,4-oxadiazol-5-yl)-3-(4-fluorophenyl)tropane (1R,2R,3S)-2-(3-Phenyl-1,2,4-oxadiazol-5-yl)-3-(4-methylphenyl)-tropane, (1R,2R,3S)-2-(3-Benzyl-1,2,4-oxadiazol-5-yl)-3-(4-fluorophenyl)tropane, (1R,2R,3S)-2-(3-(4-Phenyl-phenyl)-1,2,4-oxadiazol-5-yl)-3-(4-fluorophenyl)tropane or (1R,2R,3S)-2-(3-Phenyl-1,2,4-oxadiazol-5-yl)-3-(2-naphthyl)tropane, or or a pharmaceutically-acceptable addition salt thereof.

9. A pharmaceutical composition, comprising an effective amount of a compound of claim 7, or a pharmaceutically-acceptable addition salt thereof, together with at least one pharmaceutically-acceptable carrier or diluent.

* * * * *

UNITED STATES PATENT AND TRADEMARK OFFICE
CERTIFICATE OF CORRECTION

PATENT NO. : 5,444,070
DATED : August 22, 1995
INVENTOR(S) : Peter Moldt, Jorgen Scheel-Krüger, Leif H. Jensen It is certified that error appears in the above-indentified patent and that said Letters Patent is hereby corrected as shown below:

Column 5, line 2; "(4fluorophenyl)" should read
-- (4-fluorophenyl) --

Column 5, line 42; "3,4buty-" should read -- 3,4-buty- --
Column 7, line 50; delete the "(-" at the end of the line.
Column 7, line 51; insert the "(" at the beginning of the line
to read -- (mice,dog) --
Column 7, line 58; "macroIon" should read -- macrolon --
Column 18, line 15; "(1S2S,3R)" should read -- (1S,2S,3R) --
Column 19, line 56; "1,2,4oxadiazol" should read
-- 1,2,4-oxadiazol --
Column 20, line 3; "1,2,4oxadiazol" should read
-- 1,2,4-oxadiazol --
Column 20, line 50; insert the following -- (1R,2R,3S)-2-(3-(2-
Thienyl)-1,2,4-oxadiazol-5-yl)-3-(4-chlorophenyl)-tropane,
hydrochloride, white crystals, m.p.286°-290°C. --
Column 20, lines 53,54,& 55; delete the following "(1R,2R-
,3S840)-2-(3-(4-Pyridyl)-1,2,4-oxadiazol-5-yl)-3-(3,4-
dichlorophenyl)-tropane,dihydrochloride, white crystals
(hygroscopic),m.p.(base) 174°-184°C. --

UNITED STATES PATENT AND TRADEMARK OFFICE
CERTIFICATE OF CORRECTION

PATENT NO. : 5,444,070
DATED : August 22, 1995
INVENTOR(S) : Peter Moldt, Jorgen Scheel-Krüger, Leif H. Jensen It is certified that error appears in the above-indentified patent and that said Letters Patent is hereby corrected as shown below:

Column 34, line 26; delete "$C_{2-6}$-alkenyl," second occurrence

Column 34, line 58; "$C_{2-6}$alkenyl, $C_{2-6}$alkynyl," should read
  -- $C_{2-6}$-alkenyl, $C_{2-6}$-alkynyl, --
Column 36, line 1; "$C_{2-}$-" should read -- $C_{2-6}$- --
Column 36, line 11; "$C_{1-}$-alkoxy" should read -- $C_{1-6}$-alkoxy --

Signed and Sealed this

Nineteenth Day of December, 1995

Attest:

BRUCE LEHMAN

Attesting Officer

Commissioner of Patents and Trademarks